April 21, 1964 F. W. ANDERSON Plant Pat. 2,392
PECAN TREE
Filed March 22, 1963
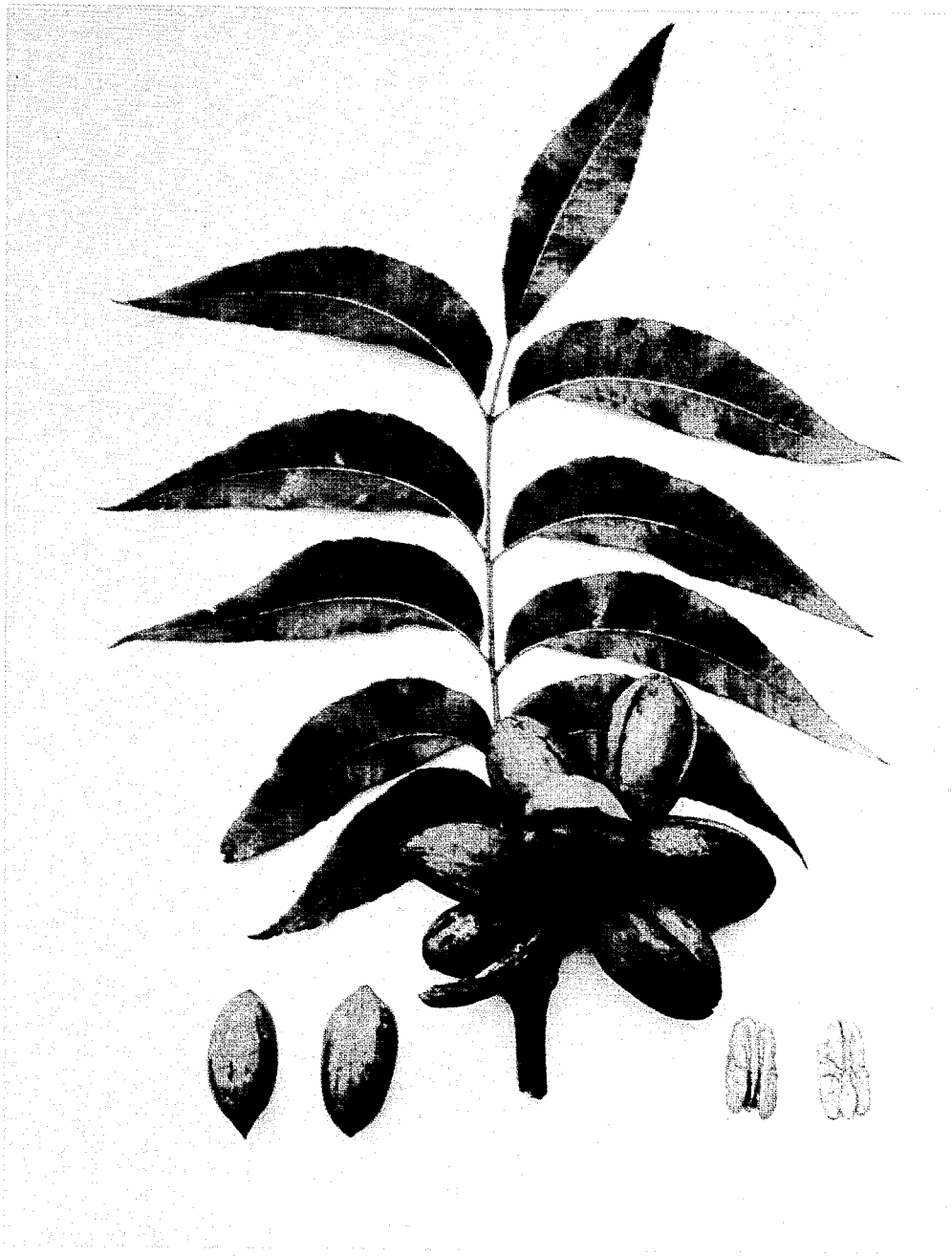
INVENTOR
Frederic W. Anderson
BY Webster & Webster
ATTYS.

United States Patent Office

Plant Pat. 2,392
Patented Apr. 21, 1964

2,392
PECAN TREE

Frederic W. Anderson, Merced, Calif., assignor to Stribling's Nurseries, Inc., Merced, Calif., a corporation of California Filed Mar. 22, 1963, Ser. No. 267,373
1 Claim. (Cl. Plt.—31)

This invention relates to a new and distinct variety of pecan tree which is particularly well adapted for commercial growing in California under its soil and climatic conditions, and especially in the area thereof known as the Central Valley.

Although pecan trees of various varieties have been tested extensively in California for many years, no wholly successful variety has been found, and as a result no important commercial pecan industry has been developed in such state. Some of the deterrent reasons are as follows:

Pecan trees of prior varieties, obtained from their native region in the southern Mississippi Valley and tested in California, did not well adapt to the growing conditions in California, usually ripening almost a month later than in such native region and which placed the trees in harvest not only in the rainy season but after most of the leaves had fallen.

Further, the trees tended to be unproductive, biennial in bearing, and the nuts often did not fill well.

Additionally, with somewhat alkaline soils, as in certain agricultural areas in California, the prior varieties of pecan trees suffered more from zinc deficiency than most fruit and nut varieties grown under like soil conditions.

It was also ascertained that, due to the relatively warm winters in California, the prior varieties also suffered from delayed foliation, and there arose varying complications in the time of bloom—with respect to the shedding of pollen and maturity of the pistils.

The herein claimed variety of pecan tree is characterized, as to novelty, by its freedom from the foregoing objectionable features of the prior varieties and by its ability to grow successfully and produce commercial crops of nuts in California.

The present variety of pecan tree is also characterized, as to novelty, by an apparent resistance to "oak root" fungus. The parent tree is growing, without evidence of "oak root" fungus infection, in an area on my ranch which was previously an almond orchard and where the trees were killed by such fungus. Also, additional trees of the present variety planted in such orchard area showed no symptoms of the disease while trees of other varieties of nuts and fruit planted in such area at the same time were seriously affected and have been almost entirely removed.

The present variety of pecan tree is further characterized, as to novelty, by early bearing of commercially satisfactory crops of well filled nuts beginning in the third year and becoming progressively greater year by year and until at least the eighth year.

The present variety of pecan tree, while having general resemblance to the seed parent Caloro (unpatented), is further characterized, as to novelty, by a tree which is more productive; by excellent-flavored nuts which are better filled; by a harvest which is approximately three weeks earlier than said Caloro; and by leaves which largely remain on the trees until after the harvest is completed and which facilitates such operation whether the nut pickup from the ground is accomplished manually or by machine. The harvest is also approximately three weeks earlier than the Stuart and the Success varieties (both unpatented).

The present variety of pecan tree was originated by me in my experimental orchard located near Le Grand, California, in the following manner:

Several thousand open pollinated pecan seedlings, resulting from planting seeds of the best previously known early ripening pecans, were brought into production under careful and continuous observation and comparison; the present variety, upon recognition by me of its distinctive features, having been selected as best for commercial growing in the Central Valley of California, or in any agricultural region of comparable soil and climatic conditions.

Subsequent to origination of the variety, as above, I asexually reproduced it by top-working on mature trees in my experimental orchard located as aforesaid, and which asexual reproductions ran true to the parent in all respects.

The drawing comprises an illustration, by photographic reproduction in color, of a cluster of nuts with a leaf; together with an illustration of nuts removed from the hulls, and a kernel split in half and shown from opposite sides.

Referring now more specifically to the botanical details of this new and distinct variety of pecan tree, the following is an outline description thereof; all major color plate identifications, by comparison with fresh specimens at approximately the time of harvest, being by reference to Maerz and Paul Dictionary of Color.

Tree:
- *Growth.*—Medium.
- *Color of bark.*—Medium.
- *Foliage.*—Dense.

Leaves:
- *Size.*—Very large.
- *Time of leafing.*—Midseason.
- *Color.*—Top side—medium green (23–L–7). Under shide—lighter green (22–L–3).

Flowering habit:
- *Age at which tree starts producing catkins.*—Very early.
- *Quantity of catkins produced.*—Abundant.
- *Size of catkins.*—Very large.
- *Time of pollen shedding.*—Early to midseason.
- *Age at which tree starts producing pistillate flowers.*—Very early.
- *Quantity of pistillate flowers produced.*—Abundant.
- *Coincidence of staminate and pistillate bloom.*—Good incidence of pollen shedding and pistillate receptivity.

Crop: Bears regularly; very heavy production.

Harvest period: Early, approximately three weeks before Caloro, Stuart, and Success; short, before leaves fall.

Nut:
- *Weight.*—Average 50–60 per pound.
- *Size.*—Average length—1⅞". Average maximum diameter—⅞".
- *Uniformity of size.*—Little variation.
- *Shape.*—Short cylindrical. Blossom end—rounded. Basal end—rounded.
- *Color of hull.*—Yellow green (21–L–8).
- *Color of shell.*—Medium brown (15–A–9).
- *Thickness of shell.*—Thin.
- *Surface of shell.*—Smooth.
- *Kernel fill.*—Very good.
- *Kernel plumpness.*—Plump.
- *Amount of kernel shrivel.*—Very little.
- *Kernel color.*—Light tan (13–K–7).
- *Flavor.*—Excellent.
- *Quality.*—Excellent.

The tree and its nuts herein described may vary in slight detail due to climatic and soil conditions under which this variety may be grown; the present description being of the variety as grown in the Central Valley of California.

The following is claimed:

A new and distinct variety of pecan tree, substantially as illustrated and described, characterized by its ability to grow successfully and to produce commercial crops of nuts under soil and climatic conditions comparable to those of the Central Valley of California; and further characterized, in comparison to the Caloro, by a regular bearing tree which is more productive, by excellent-flavored nuts which are better filled, by a harvest which is approximately three weeks earlier than said Caloro, and by leaves remaining largely on the trees until after completion of harvest; and still further characterized by a harvest which is approximately three weeks earlier than the Stuart and Success; and additionally characterized by early production, of commercially acceptable crops, beginning in the third year and becoming progressively greater year by year through at least the eighth year.

No references cited.